(12) United States Patent     (10) Patent No.:    US 8,535,366 B2
Mangiardi et al.     (45) Date of Patent:    Sep. 17, 2013

(54) IMPLANTABLE DEVICE DELIVERY SYSTEM HANDLE AND METHOD OF USE

(75) Inventors: Eric Mangiardi, Charlotte, NC (US); Jason Reynolds, Bamegal, NJ (US); Ulf Borg, Longmont, CO (US)

(73) Assignee: Merit Medical Systems, Inc., South Jordan, UT (US)

( * ) Notice: Subject to any disclaimer, the term of this patent is extended or adjusted under 35 U.S.C. 154(b) by 474 days.

(21) Appl. No.: 10/585,430

(22) PCT Filed: Jan. 7, 2005

(86) PCT No.: PCT/US2005/000515
§ 371 (c)(1),
(2), (4) Date: Jan. 7, 2009

(87) PCT Pub. No.: WO2005/070095
PCT Pub. Date: Aug. 4, 2005

(65) Prior Publication Data
US 2009/0118740 A1    May 7, 2009

Related U.S. Application Data

(60) Provisional application No. 60/534,899, filed on Jan. 8, 2004.

(51) Int. Cl.
*A61F 2/06*     (2013.01)

(52) U.S. Cl.
USPC ............................ 623/1.11; 606/194; 606/198

(58) Field of Classification Search
USPC .............. 623/1.23, 1.11, 1.12; 606/194, 198, 606/108
See application file for complete search history.

(56) References Cited

U.S. PATENT DOCUMENTS

| 5,201,757 A | * | 4/1993 | Heyn et al. ..................... 606/198 |
| 5,591,172 A | * | 1/1997 | Bachmann et al. .......... 623/1.11 |
| 5,759,186 A | * | 6/1998 | Bachmann et al. ........... 606/108 |

(Continued)

FOREIGN PATENT DOCUMENTS

| DE | 92 09 908 U1 | 9/1992 |
| DE | 43 23 866 A1 | 1/1994 |

(Continued)

OTHER PUBLICATIONS

Supplementary European Search Report for EP Application No. 05705271.4, dated May 4, 2007.

(Continued)

*Primary Examiner* — Gary Jackson
*Assistant Examiner* — Katrina Stransky
(74) *Attorney, Agent, or Firm* — Stoel Rives LLP (57) ABSTRACT

The present invention, in an exemplary embodiment, provides a delivery system and novel handle configuration for the delivery system that facilitates repeatable placement of implantable devices. In particular, in optical embodiments, the handle allows for the reversible coupling of scopes directly to the handle to enhance physician control during placement. The delivery system also allows for one-handed manipulation as finger action can be used to engage and disengage the scope as well as actuate the extent of implantable device deployment. Exemplary delivery systems are flexible, durable and/or assure proper installation of one or more implantable devices in a single procedure. Moreover, the preferred embodiments of the delivery system provides for the reloading of the delivery device with additional implantable devices for additional interventional procedures, resulting in a substantially reusable delivery device.

28 Claims, 4 Drawing Sheets

(56) References Cited

U.S. PATENT DOCUMENTS

| | | | |
|---|---|---|---|
| 5,824,041 A | 10/1998 | Lenker et al. | |
| 5,868,755 A | 2/1999 | Kanner et al. | |
| 5,954,729 A * | 9/1999 | Bachmann et al. | 606/108 |
| 6,093,194 A * | 7/2000 | Mikus et al. | 606/108 |
| 6,143,021 A * | 11/2000 | Staehle | 623/1.11 |
| 6,162,231 A | 12/2000 | Mikus et al. | |
| 6,383,211 B1 * | 5/2002 | Staehle | 623/1.11 |
| 6,391,051 B2 | 5/2002 | Sullivan, III et al. | |
| 6,413,269 B1 * | 7/2002 | Bui et al. | 623/1.11 |
| 6,428,566 B1 | 8/2002 | Holt | |
| 6,514,261 B1 | 2/2003 | Randall et al. | |
| 6,669,719 B2 | 12/2003 | Wallace et al. | |
| 6,726,712 B1 | 4/2004 | Raeder-Devens et al. | |
| 6,866,669 B2 | 3/2005 | Buzzard et al. | |
| 6,926,732 B2 * | 8/2005 | Derus et al. | 623/1.12 |
| 7,731,654 B2 | 6/2010 | Mangiardi et al. | |
| 2002/0151967 A1 * | 10/2002 | Mikus et al. | 623/1.22 |
| 2002/0183827 A1 * | 12/2002 | Derus et al. | 623/1.12 |
| 2003/0050686 A1 | 3/2003 | Raeder-Devens et al. | |
| 2003/0167060 A1 * | 9/2003 | Buzzard et al. | 606/108 |
| 2004/0193243 A1 | 9/2004 | Mangiardi et al. | |
| 2004/0267281 A1 | 12/2004 | Harari et al. | |
| 2005/0090887 A1 * | 4/2005 | Pryor | 623/1.11 |
| 2005/0125050 A1 | 6/2005 | Carter et al. | |
| 2005/0149160 A1 | 7/2005 | McFerran | |
| 2005/0278010 A1 | 12/2005 | Richardson | |
| 2007/0043421 A1 | 2/2007 | Mangiardi et al. | |
| 2007/0100421 A1 | 5/2007 | Griffin | |
| 2007/0208350 A1 | 9/2007 | Gunderson | |
| 2010/0049295 A1 | 2/2010 | Satasiya et al. | |

FOREIGN PATENT DOCUMENTS

| | | |
|---|---|---|
| EP | 0 364 420 A | 4/1990 |
| EP | 0 872 220 A1 | 10/1998 |
| WO | WO 96/31174 | 10/1996 |
| WO | WO 00/78246 | 12/2000 |
| WO | WO-00/78246 A2 | 12/2000 |
| WO | WO 02/087470 | 11/2002 |
| WO | WO 03/090644 | 11/2003 |
| WO | WO 2004/030571 | 4/2004 |
| WO | WO 2005/070095 | 8/2005 |
| WO | WO 2008/042266 | 4/2008 |
| WO | PCT/US2012/062603 | 10/2012 |

OTHER PUBLICATIONS

PCT Notification of Transmittal of the International Search Report and the Written Opinion of The International Searching Authority, or the Declaration, mailed Sep. 28, 2005 for PCT/US2005/00515 (Filed Jan. 7, 2005).
PCT Notification of Transmittal of the International Search Report and Written Opinion dated Nov. 23, 2006 for PCT/US2006/018811.
International Search Report and Written Opinion for PCT/US2009/052691 dated Oct. 29, 2009.
Office Action for U.S. Appl. No. 11/432,964 dated Jul. 9, 2009.
Office Action for U.S. Appl. No. 11/432,964 dated Dec. 7, 2009.
International Search Report and Written Opinion for PCT/US05/00515 dated Aug. 4, 2005.
Restriction Requirement dated Mar. 6, 2012 for U.S. Appl. No. 12/535,980.
Office Action dated May 25, 2012 for U.S. Appl. No. 12/535,980.
Office Action dated Jan. 31, 2012 for U.S. Appl. No. 10/585,430.
U.S. Appl. No. 13/313,929, filed Oct. 30, 2012, Robinson.
U.S. Appl. No. 13/664,137, filed Oct. 30, 2012, Robinson.
U.S. Appl. No. 13/664,200, filed Oct. 30, 2012, Robinson.
U.S. Appl. No. 13/664,234, filed Oct. 30, 2012, Robinson.
U.S. Appl. No. 13/664,267, filed Oct. 30, 2012, Robinson.
Office Action dated Nov. 14, 2012 for U.S. Appl. No. 12/535,980.
International Publication and Search Report dated Feb. 25, 2012 for WO10021836.
International Publication and Search Report dated Aug. 4, 2005 for WO2005070095.
International Publication and Search Report dated Jun. 14, 2012 for WO2012078794.

* cited by examiner

IMPLANTABLE DEVICE DELIVERY SYSTEM HANDLE AND METHOD OF USE

FIELD OF INVENTION

The present invention relates generally to delivery systems directed to implantable medical devices and more particularly to specialized handles for allowing scope introduction and locking and one-hand implantable device placement and delivery.

BACKGROUND OF THE INVENTION

Interventional practitioners, regardless of subspecialty have always had to demonstrate profound dexterity in order to effectively and accurately perform invasive procedures. This is particularly the case with the delivery and deployment of implantable devices where there is very little room for error with respect to placement. In order to assist with placement accuracy, many interventionalists utilize scopes, such as bronchoscopes. Unfortunately, handling the scope and the delivery catheter can often be a clumsy process when the two devices easily disassociate from each other. Moreover, since many delivery catheters, for one reason or another, cannot be adequately managed with one hand, additional personnel are required when handling the scope and the delivery catheter.

Therefore, there is an existing need for an ergonomic handle specifically, and a delivery system generally, that allows a physician to deploy an implantable device with one hand. Moreover, the need remains for a delivery system that can receive a scope and lock the scope relative to the delivery system to give the physician greater control of the delivery and deployment of implantable devices.

SUMMARY OF EXEMPLARY EMBODIMENTS

According to the present invention, a device is provided for allowing a user to deploy a stent in an anatomical lumen of a patient. The stent deployment device comprises a stabilizing member, a longitudinally extending outer tubular member having distal and proximal ends, and a longitudinally extending inner tubular member having distal and proximal ends, the distal end of the inner tubular member comprising a tip. The inner tubular member is coupled with the stabilizing member and at least a portion of the inner tubular member is disposed within the outer tubular member such that the inner tubular member is longitudinally and axially displaceable relative to the outer tubular member. A deployment mechanism is coupled with the outer tubular member. The deployment mechanism comprises a release member for longitudinally moving the outer tubular member relative to the inner tubular member.

Also according to the present invention, a stent delivery system is provided for use in an anatomical lumen of a patient. The stent delivery system comprises a stabilizing member, a longitudinally extending outer tubular member having distal and proximal ends, and a longitudinally extending inner tubular member having distal and proximal ends, the distal end of the inner tubular member comprising a tip. The inner tubular member is coupled with the stabilizing member and at least a portion of the inner tubular member is disposed within the outer tubular member such that the inner tubular member is longitudinally and axially displaceable relative to the outer tubular member. A stent having a proximal end and a distal end is slidably disposed in the outer tubular member. A deployment mechanism is coupled with the outer tubular member. The deployment mechanism comprises a release member for longitudinally moving the outer tubular member in a direction toward the stabilizing member relative to the inner tubular member. The tip of the inner tubular member engages the proximal end of the stent for advancing the stent toward the distal end of the outer tubular member as the release member moves toward the stabilizing member.

Further according to the present invention, a method for delivering a stent in an anatomical lumen of a patient. The method of stent delivery comprises the steps of providing a delivery device including a stabilizing member, a longitudinally extending outer tubular member having distal and proximal ends, and a longitudinally extending inner tubular member having distal and proximal ends, the distal end of the inner tubular member comprising a tip. The inner tubular member is coupled with the stabilizing member and at least a portion of the inner tubular member is disposed within the outer tubular member such that the inner tubular member is longitudinally and axially displaceable relative to the outer tubular member. A deployment mechanism is coupled with the outer tubular member. The deployment mechanism comprises a release member for longitudinally moving the outer tubular member relative to the inner tubular member. The method of stent delivery according to the present invention further comprises the steps of slidably disposing a stent having a proximal end and a distal end in the outer tubular member, and advancing the release member and the outer tubular member relative to the inner tubular member in a direction toward the stabilizing member. The tip of the inner tubular member engages the proximal end of the stent for advancing the stent toward the distal end of the outer tubular member as the release member moves toward the stabilizing member.

It is a principal purpose of the present invention to provide a delivery system for implantable devices that facilitates ease and accuracy of deployment. In accordance with an exemplary embodiment of the present invention, a delivery system is provided that allows the physician to concentrate on correct placement without having to estimate extent of deployment. In particular, in a preferred embodiment, the present device has a physical safety mechanism that limits deployment to the critical deployment point (e.g., predetermined length proportional to the length of the implantable device being deployed). The critical deployment point may range from 5% to 95% of the implantable devices length and the optimal length is relative based on the length of the implantable device. At this point, if the physician is satisfied with placement, she can engage the safety means to what we refer to as the Proceed Orientation (PO) and fully deploy the implantable medical appliance. Alternative safety systems in accordance with the invention include but are not limited to removable tab stops, ratchet incremental stops, etc., that allow for deployment and implantable device realignment along a continuum.

Another objective of an exemplary embodiment in accordance with the present invention is to provide a delivery system that allows for the one handed placement of large implantable devices generally and stents of about 50 mm or larger, in particular.

Still another objective in accordance with a preferred embodiment of the present invention is to provide a delivery device having direct visualization capabilities directly incorporated into the device by allowing for the passage of the scope through the internal diameter of the delivery device.

Yet another objective in accordance with an exemplary embodiment of the present invention is to provide a delivery system handle that releasably engages the scope lumen in order to provide enhanced physician control. In line with this objective, preferred embodiments facilitate the user's ability to tighten and loosen the scope with the same hand that actuates the safety mechanism by making the respective items available to different phalanges of the users hand.

In addition to the above objectives, an exemplary deployment system preferably has one or more of the following characteristics: (1) biocompatible; (2) compliant with specialized radially expanding implantable devices; (3) capable of distal or proximal medical appliance release; (4) smooth and clean outer surface; (5) length of the device variable according to the insertion procedure to be employed; (6) outer dimension as small as possible (depends on the diameter of crimped medical appliance); (7) dimensions of the device must offer enough space for the crimped implantable devices; (8) sufficient flexibility to adapt to anatomical curvatures without loss of ability to push or pull; (9) low friction between the moving parts; (10) sufficient resistance to kinking; (11) good deployment force, ability to reposition partially deployed medical appliance; and (12) sufficiently economical to manufacture so as to make the deployment apparatus disposable.

Further objectives, features and advantages of the invention will be apparent from the following detailed description taken in conjunction with the accompanying drawings.

BRIEF DESCRIPTION OF THE FIGURES

FIG. 3 shows a perspective view, of the proximal region of FIG. 1, of an exemplary delivery system in accordance with the present invention showing the deployment system 100 comprising a first release member 200 and second release member 300, wherein the first release member 200 and the second release member 300 have been retracted proximally toward the support member 400 to fully deploy a large implantable device.

FIG. 4 shows the proximal region thereof. In particular, a preferred scope coupling system is shown at the proximal most area of the delivery system wherein the scope lumen feeds through into the interior of the delivery system. The coupling system in this embodiment comprises a rotationally adjustable clamp that allows for the tightening and/or loosening of the delivery system with respect to the scope. It is also shown that the outer tube, interchangeably referred to as the outer sheath, is disassociatable with respect to the handle and the inner tube such that the outer tube is a functional component of implantable device deployment. In the deliverable or commercially available configuration, the outer tube is provided at a predetermined distance distal the handle body. The predetermined distance is a function at least in part of the length of the implantable device and/or the length required to fully deploy the implantable device. Along that continuum between the handle and the slide grip of the outer tube is a point or points, short of full deployment, at which the outer tube can be retracted while allowing the physician to readjust the implantable device. As the outer sheath is retracted proximally toward the handle body, the implantable device is exposed and partially deployed. The scope coupling member is retained while providing an alternative deployment mechanism. In this embodiment, a pull handle is provided that is part of a pulley system for moving the outer tube proximally with respect to the inner tube and/or the implantable device. The outer sheath guide is provided to house the outer sheath pulley system proximal to the portion of the outer tube that is delivered into the patient.

DETAILED DESCRIPTION OF AN EMBODIMENT

The present invention, in a preferred embodiment, provides an implantable device delivery system that allows the user to install an implantable device with one hand. Specifically, implantable devices may be broadly interpreted to include stents or other therapeutic medical appliances but are preferably devices like the Stent Technology System (STS) family of devices developed by Alveolus®; which includes implantable devices developed in accordance with U.S. patent application Ser. Nos. 10/190,770, 10/288,615, and 60/493,402 and international patent application Ser. No. PCT/DE02/01244, which are incorporated in their entirety by this reference. In either case the preferred delivery system is preferably formed of a material that allows for sterilization.

The distal end of the device may be configured such that a portion of the distal region is removable, preferably including the distal portions of the tracks such that a housing containing additional therapeutic medical appliances can be coupled with the device to form a reloadable delivery device. Alternatively, the device may be reloaded with a single appliance containing distal tip, which can be screwed onto the device or coupled with the device by other conventional means. In either instance, the preferred device is made of a sterilizable material that allows the device to be reused.

In optical delivery system embodiments, the system comprises inner and outer tubular members that are longitudinally and axially disassociatable with respect to one another and a handle preferably coupled with a portion of the inner tubular member and that has a scope coupling mechanism. In certain embodiments a slide grip is also coupled with a portion of the outer tubular member such that when the delivery system is in use the user thereof can disassociate the outer tubular member with respect to the handle and/or the inner tubular member by moving the outer tubular member distally or proximally with respect to the handle and/or inner tubular member. In additional embodiments there is a distal tip coupled with the distal portion of the inner tubular member, which is at the opposite end of the inner tubular member as the handle. An advantage of certain embodiments of the present handle design is the ability to manipulate the scope (e.g., rotate) with respect to the handle when the scope and handle are engaged.

Figure 4:
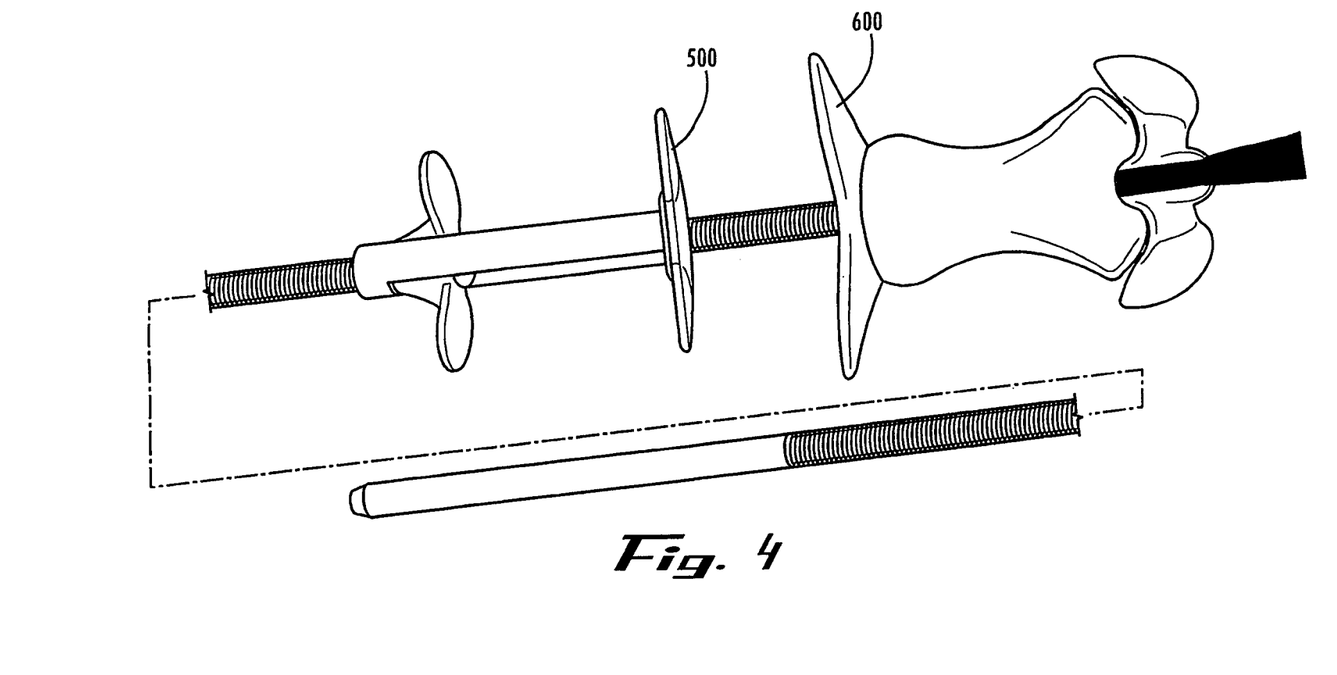

In an embodiment not shown in FIG. 4, the scope can be locked in communication with the handle by alternative means than the rotational clamp. In alternative embodiments, a slide switch, clamp, threaded engagement or other conventional means may be employed. Additionally, alternative safety mechanisms include but are not limited to removable tabs that couple with and are removable from the inner tubular member exposed between the slide grip and the handle body. The length of the removable tab would be roughly the length necessary to allow the outer tubular member to be retracted to the critical deployment point. In such embodiments, full deployment is achieved by removing the tab and continuing the proximal movement of the outer tubular member with respect to the handle. The tab may be coupled with the tube in a reversible manner such as form fitting around a portion thereof.

Figure 1:
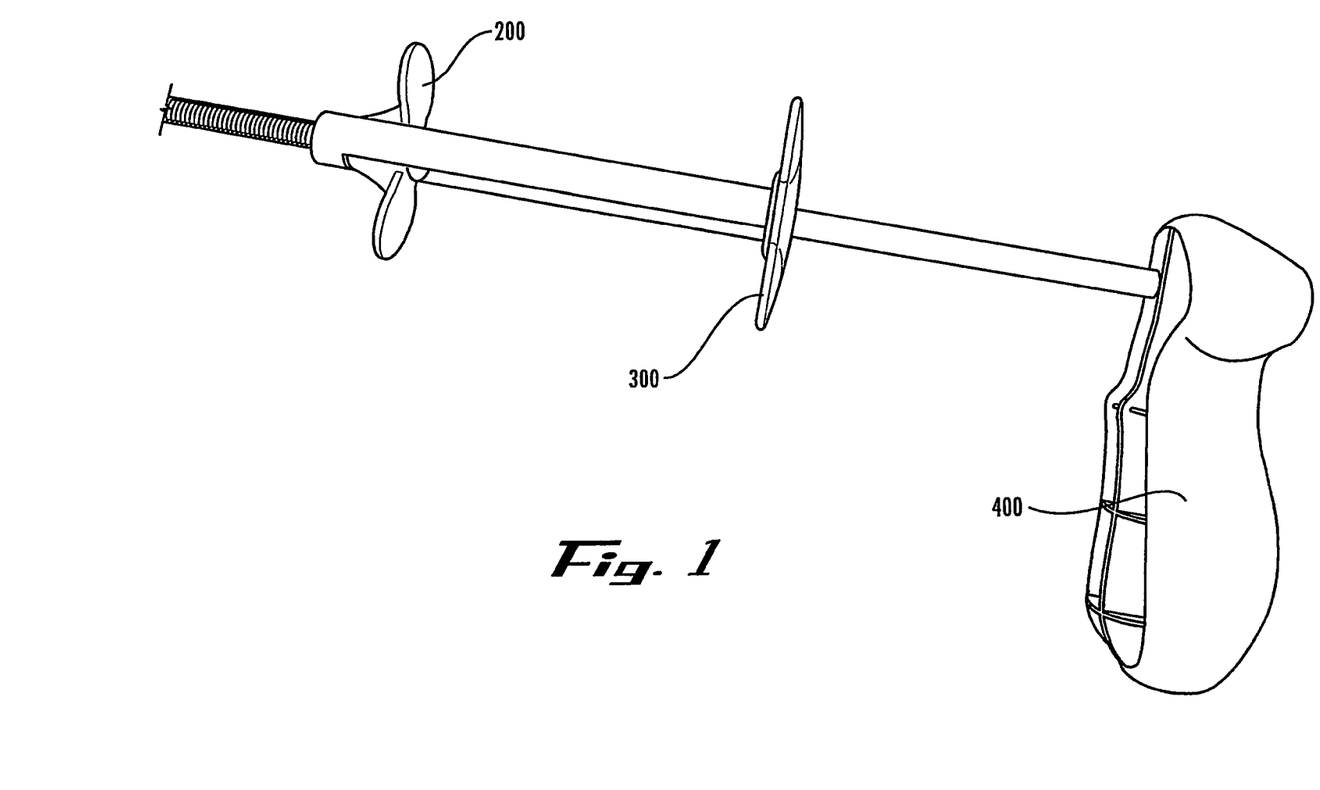
FIG. 1 shows a perspective view of the proximal region of an exemplary delivery system in accordance with the present invention showing the deployment system 100 comprising a first release member 200 and second release member 300 that allow for staged release of an implantable device by proportionally retracting the outer tubular member, the deployment system 100 in a pre-deployment configuration.
Figure 2:
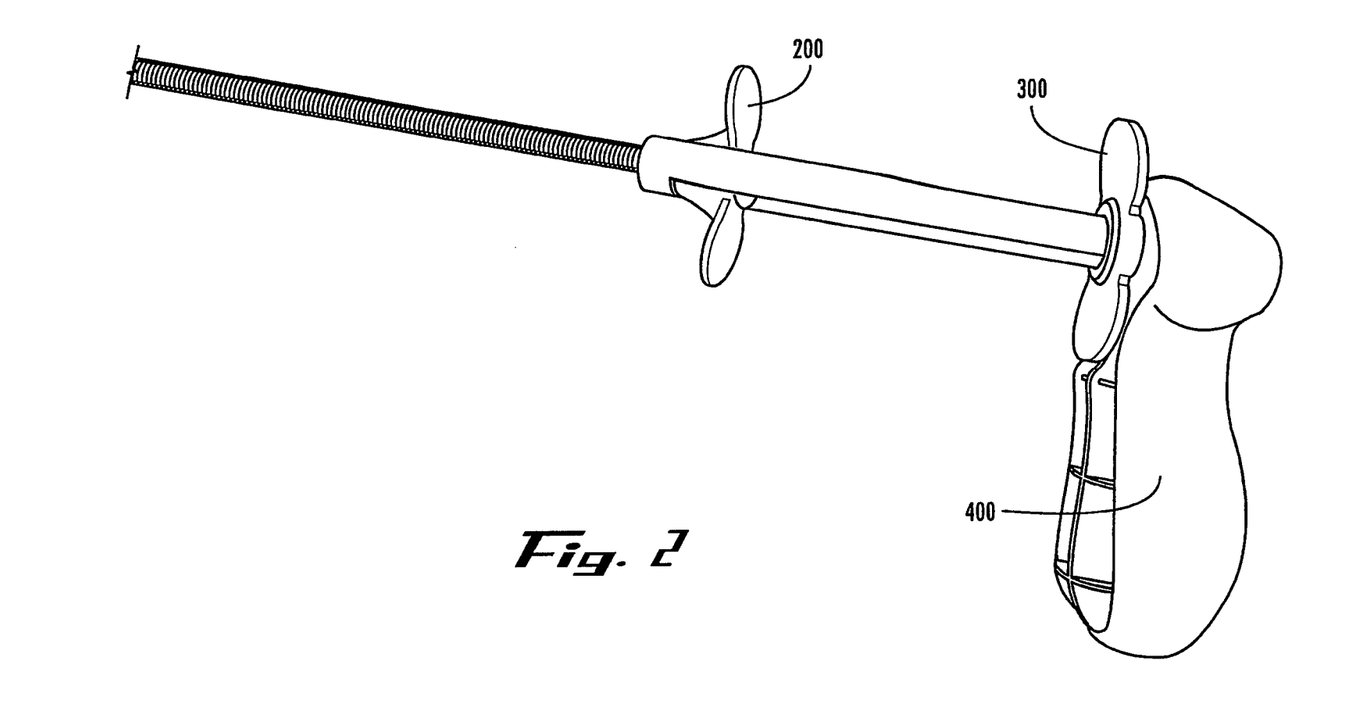
FIG. 2 shows a perspective view, of the proximal region of FIG. 1, of an exemplary delivery system in accordance with the present invention showing the deployment system 100 comprising a first release member 200 and second release member 300, wherein the second release member 300 has been retracted proximally toward the support member 400 to partially deploy a large implantable device.

In over the guidewire embodiments, the devices have a similar construction as the optical, with a significantly smaller ID. The outer and inner tubular members specifically and the catheter generally incorporate many of the features of the delivery systems developed by Alveolus®, like those disclosed in U.S. patent application Ser. Nos. 10/281,429 and 10/404,197 which are incorporated in their entirety by this reference. A principal distinction between the present catheter and that disclosed in the U.S. patent application Ser. No. 10/281,429 application is the substitution of the deployment system for the safety mechanism. Referring specifically to FIGS. 1-3, it can be seen that a user of the instant device can rest her palm against the back support member 400 and retract serially the first and second release members 200 and 300. The order of retraction is preferably the second release member 300 then the first release member 200, however, order of retraction can vary. Moreover, both may be retracted at once. As the release members 200 and 300 are retracted proximally toward the support member 400, the outer sheath is retracted and the implantable device is deployed. Because this is a proportional release system, only one release member 200 is necessary with implantable devices that are less than about 50 mm. Implantable devices above this range are considered "large" or "larger" implantable devices. A deployment system with a single release member 200 resembles that shown in FIG. 4. In a guidewire version, the catheter dimensions would vary.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A stent deployment device for allowing a user to deploy a stent in an anatomical lumen of a patient, the stent deployment device comprising:
   a support member configured to abut against a palm of a hand of the user;
   a longitudinally extending outer tubular member having distal and proximal ends along a longitudinal axis, the distal end configured to receive the stent such that the stent is slidably disposed in the outer tubular member;
   a longitudinally extending inner tubular member having distal and proximal ends, the distal end of the inner tubular member comprising a tip, the inner tubular member coupled with the support member and at least a portion of the inner tubular member disposed within the outer tubular member such that the inner tubular member is longitudinally and axially displaceable relative to the outer tubular member; and
   a deployment mechanism coupled with the outer tubular member and configured to allow staged release of the stent, the deployment mechanism comprising
      a graspable first release member to at least partially move the outer tubular member proximally and longitudinally relative to the inner tubular member, and
      a graspable second release member positioned proximal to the first release member and operably connected to the first release member to move the outer tubular member proximally and longitudinally relative to the inner tubular member,
   wherein the first release member is slidable along the longitudinal axis and has a first flange extending transverse to the longitudinal axis, and the second release member is slidable along the longitudinal axis and has a second flange extending transverse to the longitudinal axis, and
   wherein the first release member and the second release member are configured to be serially retracted to provide staged release of the stent such that slidably retracting the second release member moves the first release member and the outer tubular member proximally and longitudinally relative to the inner tubular member from a first position to a second position to partially deploy the stent, and wherein subsequent sliding retraction of the first release member moves the outer tubular member proximally and longitudinally relative to the inner tubular member from the second position to a third position to fully deploy the stent.

2. The stent deployment device as recited in claim 1, further comprising a safety member for preventing movement of the first release member and the outer tubular member toward the support member beyond a predetermined position of the outer tubular member relative to the inner tubular member.

3. The stent deployment device as recited in claim 2, wherein movement of the first release member from the first position to the predetermined position exposes at least a portion of the stent.

4. The stent deployment device as recited in claim 3, wherein the portion of the stent exposed is from about 5% to about 95% of the length of the stent.

5. The stent deployment device as recited in claim 2, wherein the safety member comprises a removable tab disposed between the support member and the outer tubular member.

6. The stent deployment device as recited in claim 1, further comprising an elongated viewing device having a proximal end and distal end, the viewing device slidably disposed in the outer tubular member such that the proximal end of the viewing device extends outwardly of the proximal end of the outer tubular member.

7. The stent deployment device as recited in claim 6, further comprising means for releasably securing the viewing device with respect to the outer tubular member.

8. The stent deployment device as recited in claim 7, wherein the viewing device securing means is associated with the support member.

9. The stent deployment device as recited in claim 8, wherein the viewing device securing means comprises a clamp head threadably received in the support member.

10. A stent delivery system for use in an anatomical lumen of a patient, the stent delivery system comprising:
   a support member configured to abut against a palm of a hand of the user;
   a longitudinally extending outer tubular member having distal and proximal ends along a longitudinal axis, the distal end configured to receive the stent such that the stent is slidably disposed in the outer tubular member;
   a longitudinally extending inner tubular member having distal and proximal ends, the distal end of the inner tubular member comprising a tip, the inner tubular member coupled with the support member and at least a portion of the inner tubular member disposed within the outer tubular member such that the inner tubular member is longitudinally and axially displaceable relative to the outer tubular member;

a stent having a proximal end and a distal end and slidably disposed within a distal portion of the outer tubular member and around a distal portion of the inner tubular member; and a deployment mechanism coupled with the outer tubular member and configured to allow staged release of the stent, the deployment mechanism comprising a graspable first release member to at least partially move the outer tubular member proximally and longitudinally relative to the inner tubular member, and a graspable second release member positioned proximal to the first release member and operably connected to the first release member to move the outer tubular member proximally and longitudinally relative to the inner tubular member, wherein the first release member is slidable along the longitudinal axis and has a first flange extending transverse to the longitudinal axis, and the second release member is slidable along the longitudinal axis and has a second flange extending transverse to the longitudinal axis, and wherein the tip of the inner tubular member engages the proximal end of the stent for advancing the stent toward the distal end of the outer tubular member as the first and second release members move toward the support member, and wherein the first release member and the second release member are configured to be serially retracted to provide staged release of the stent such that slidably retracting the second release member moves the first release member and the outer tubular member proximally and longitudinally relative to the inner tubular member from a first position to a second position to partially deploy the stent, and wherein subsequent sliding retraction of the first release member moves the outer tubular member proximally and longitudinally relative to the inner tubular member from the second position to a third position to fully deploy the stent.

11. The stent delivery system as recited in claim 10, wherein a portion of the stent is exposed outwardly of the distal end of the outer tubular member.

12. The stent delivery system as recited in claim 11, wherein the stent is deployed from the distal end of the outer tubular member.

13. The stent delivery system as recited in claim 10, further comprising a safety member for preventing movement of the first release member and the outer tubular member toward the support member beyond a predetermined position of the outer tubular member relative to the inner tubular member.

14. The stent delivery system as recited in claim 13, wherein movement of the first release member from the first position of the outer tubular member relative to the inner tubular member to the predetermined position exposes at least a portion of the stent outwardly of the distal end of the outer tubular member.

15. The stent delivery system as recited in claim 14, wherein the portion of the stent exposed is from about 5% to about 95% of the length of the stent.

16. The stent delivery system as recited in claim 13, wherein the safety member comprises a removable tab disposed between the support member and the outer tubular member.

17. The stent delivery system as recited in claim 10, further comprising an elongated viewing device having a proximal end and distal end, the viewing device slidably disposed in the outer tubular member such that the proximal end of the viewing device extends outwardly of the proximal end of the outer tubular member.

18. The stent delivery system as recited in claim 17, further comprising means for releasably securing the viewing device with respect to the outer tubular member.

19. The stent delivery system as recited in claim 18, wherein the viewing device securing means is associated with the support member.

20. The stent deployment device as recited in claim 19, wherein the viewing device securing means comprises a clamp threadably received in the support member.

21. A method for delivering a stent in an anatomical lumen of a patient, the method of stent delivery comprising:

providing a delivery device including a support member configured to abut against a palm of a hand of the user, a longitudinally extending outer tubular member having distal and proximal ends along a longitudinal axis, the distal end configured to receive the stent such that the stent is slidably disposed within the outer tubular member, a longitudinally extending inner tubular member having distal and proximal ends, the distal end of the inner tubular member comprising a tip, the inner tubular member coupled with the support member and at least a portion of the inner tubular member disposed within the outer tubular member such that the inner tubular member is longitudinally and axially displaceable relative to the outer tubular member, and a deployment mechanism coupled with the outer tubular member and configured to allow staged release of the stent, the deployment mechanism comprising a graspable first release member to at least partially move the outer tubular member proximally and longitudinally relative to the inner tubular member, and a graspable second release member positioned proximal to the first release member and operably connected to the first release member to move the outer tubular member proximally and longitudinally relative to the inner tubular member, wherein the first release member is slidable along the longitudinal axis and has a first flange extending transverse to the longitudinal axis, and the second release member is slidable along the longitudinal axis and has a second flange extending transverse to the longitudinal axis, and wherein the first release member and the second release member are configured to be serially retracted to provide staged deployment of the stent, slidably disposing a stent having a proximal end and a distal end within a distal portion of the outer tubular member and around a distal portion of the inner tubular member, wherein the tip of the inner tubular member engages the proximal end of the stent to advance the stent toward the distal end of the outer tubular member as the outer tubular member moves toward the support member relative to the inner tubular member;

positioning the distal portion of the outer tubular member within the anatomical lumen of the patient at a desired location;

slidably retracting the second release member in a direction toward the support member to thereby retract the first release member and the outer tubular member relative to the inner tubular member from a first position to a second position to partially deploy the distal end of the stent; and slidably retracting the first release member in a direction toward the support member and toward the second release member to thereby retract the outer tubular member relative to the inner tubular member from the second position to a third position to completely deploy the stent in the anatomical lumen of the patient.

22. The method of stent delivery as recited in claim 21, wherein a portion of the stent is exposed outwardly of the distal end of the outer tubular member.

23. The method of stent delivery as recited in claim 22, wherein the stent is deployed from the distal end of the outer tubular member.

24. The method of stent delivery as recited in claim 21, further comprising preventing movement of the first release member and the outer tubular member toward the support member beyond a predetermined position of the outer tubular member relative to the inner tubular member.

25. The method of stent delivery as recited in claim 21, further comprising providing an elongated viewing device having a proximal end and distal end, and slidably disposing the viewing device in the outer tubular member such that the proximal end of the viewing device extends outwardly of the proximal end of the outer tubular member.

26. The stent delivery system as recited in claim 25, further comprising releasably securing the viewing device with respect to the outer tubular member.

27. The stent deployment device as recited in claim 1, wherein the deployment mechanism is operable without initially disengaging a safety mechanism.

28. A stent deployment device for allowing a user to deploy a stent in an anatomical lumen of a patient, the stent deployment device comprising:

a support member configured to abut against a palm of a hand of the user;

a longitudinally extending outer tubular member having distal and proximal ends along a longitudinal axis, the distal end configured to receive the stent such that the stent is slidably disposed in the outer tubular member;

a longitudinally extending inner tubular member having distal and proximal ends, the distal end of the inner tubular member comprising a tip, the inner tubular member coupled with the support member and at least a portion of the inner tubular member disposed within the outer tubular member such that the inner tubular member is longitudinally and axially displaceable relative to the outer tubular member; and a deployment mechanism coupled with the outer tubular member and configured to allow staged release of the stent, the deployment mechanism comprising a graspable first release member configured to retract proximally and longitudinally with respect to the inner tubular member and configured to at least partially move the outer tubular member proximally and longitudinally relative to the inner tubular member, and a graspable second release member positioned proximal to the first release member and operably connected to the first release member, the second release member configured to retract proximally and longitudinally with respect to the inner tubular member and configured to move the outer tubular member proximally and longitudinally relative to the inner tubular member, wherein the first release member is slidable along the longitudinal axis and has a first flange extending transverse to the longitudinal axis, and the second release member is slidable along the longitudinal axis and has a second flange extending transverse to the longitudinal axis, and wherein the first release member and the second release member are configured to be serially retracted to provide staged release of the stent such that slidably retracting the second release member proximally and longitudinally with respect to the inner tubular member moves the first release member and the outer tubular member proximally and longitudinally relative to the inner tubular member from a first position to a second position to partially deploy the stent, and wherein subsequent sliding retraction of the first release member proximally and longitudinally with respect to the inner tubular member moves the outer tubular member proximally and longitudinally relative to the inner tubular member from the second position to a third position to fully deploy the stent.

* * * * *

UNITED STATES PATENT AND TRADEMARK OFFICE
CERTIFICATE OF CORRECTION

PATENT NO.         : 8,535,366 B2                                                                 Page 1 of 1
APPLICATION NO. : 10/585430
DATED              : September 17, 2013
INVENTOR(S)        : Mangiardi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1219 days.

Signed and Sealed this

Fifteenth Day of September, 2015

Michelle K. Lee
*Director of the United States Patent and Trademark Office*